United States Patent [19]
Goldberg et al.

[11] Patent Number: 5,356,386
[45] Date of Patent: * Oct. 18, 1994

[54] APPARATUS FOR LOCATING BODY CAVITIES

[75] Inventors: Edward M. Goldberg, Glencoe; Lev Melinyshyn, Mt. Prospect; Michael Jaron, Des Plaines; Jeffrey M. Stupar, Chicago, all of Ill.

[73] Assignee: Uresil Corporation, Skokie, Ill.

[ * ] Notice: The portion of the term of this patent subsequent to May 31, 2005 has been disclaimed.

[21] Appl. No.: 924,407

[22] Filed: Aug. 3, 1992

Related U.S. Application Data

[60] Continuation of Ser. No. 559,757, Jul. 30, 1990, abandoned, which is a division of Ser. No. 310,366, Feb. 13, 1989, Pat. No. 4,944,724, which is a continuation of Ser. No. 58,400, Jun. 5, 1987, abandoned.

[51] Int. Cl.⁵ .................................................. A61M 1/00
[52] U.S. Cl. ..................................... 604/118; 604/323
[58] Field of Search ............... 604/118, 318, 319, 320, 604/323

[56] References Cited

U.S. PATENT DOCUMENTS

| 4,015,603 | 4/1977 | Kurtz et al. | 604/318 |
| 4,063,556 | 12/1977 | Thomas et al. | 604/318 |
| 4,543,095 | 9/1985 | Jensen | 604/318 |
| 4,820,284 | 4/1989 | Hauri | 604/318 |
| 4,944,724 | 7/1990 | Goldberg et al. | 604/118 |

Primary Examiner—Paul J. Hirsch
Attorney, Agent, or Firm—Laff, Whitesel, Conte & Saret

[57] ABSTRACT

An apparatus for locating a body cavity having a fluctuating fluid pressure by signaling the fluctuating pressure when the cavity is entered and then transporting fluid either into or out of the cavity.

15 Claims, 2 Drawing Sheets

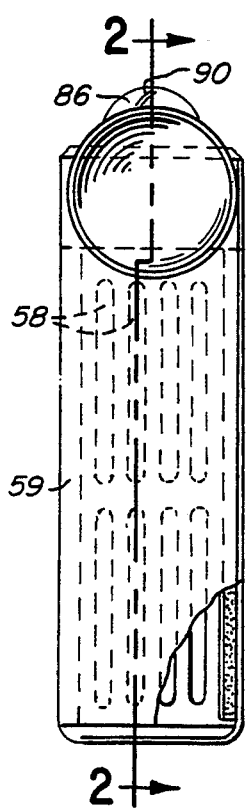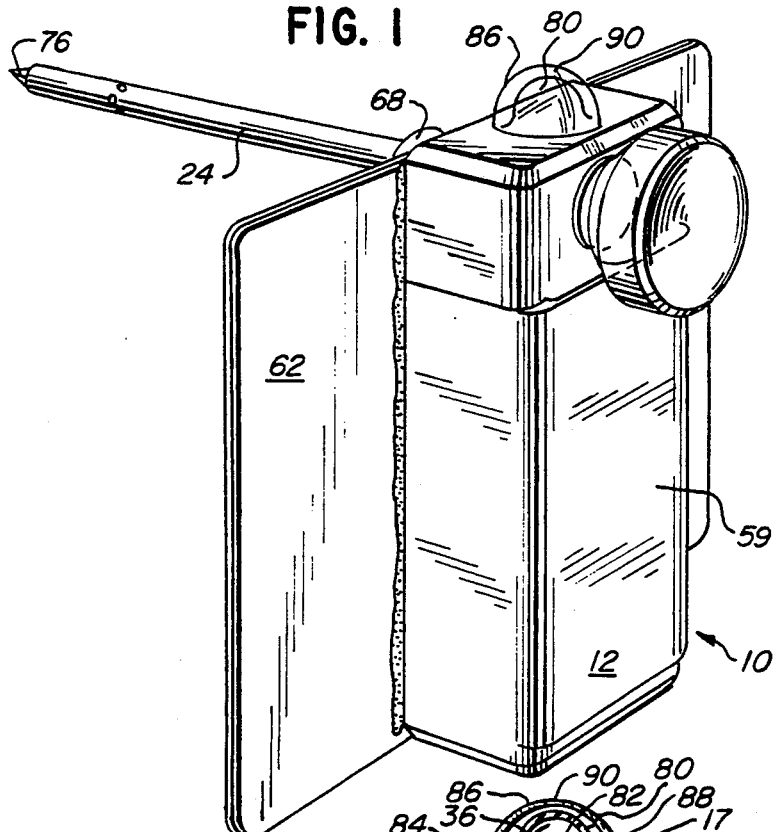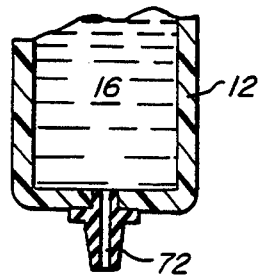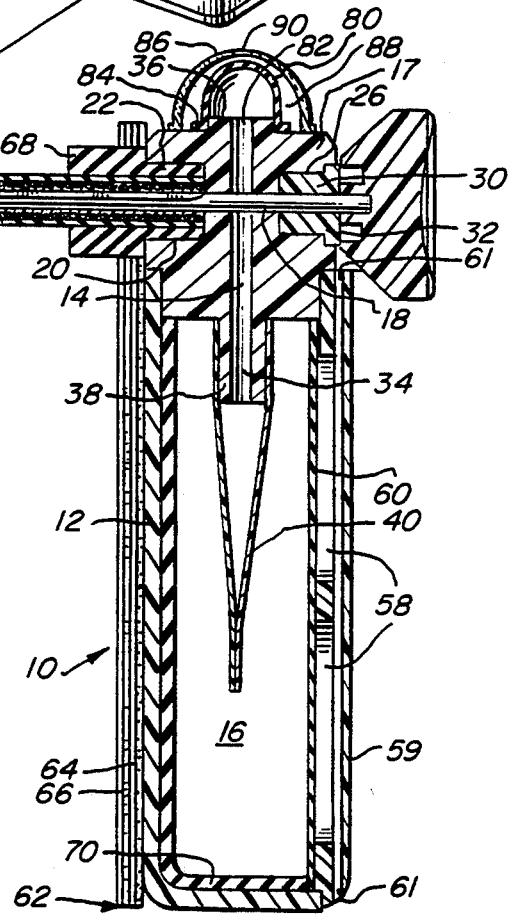

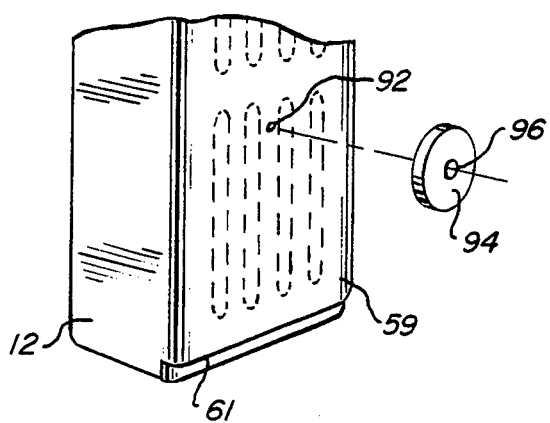
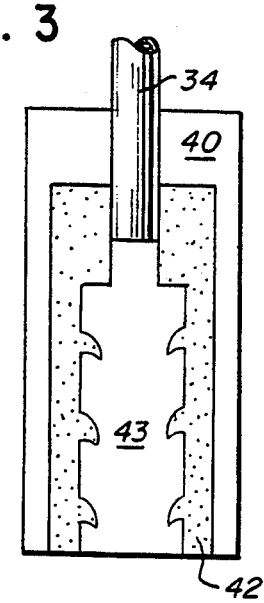
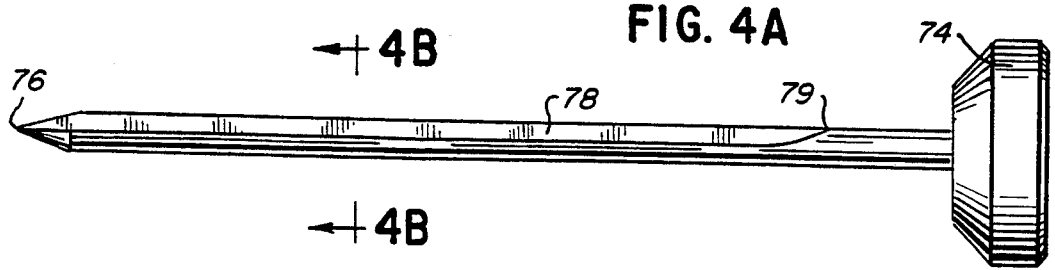
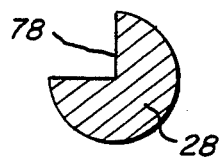
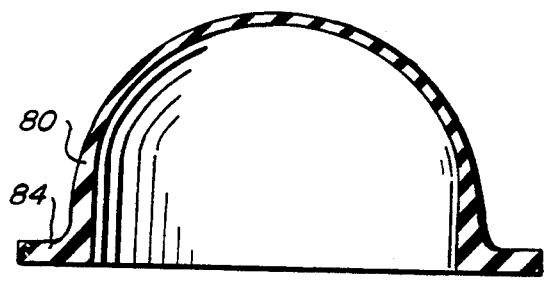
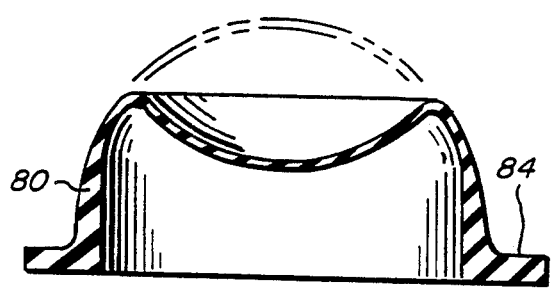

APPARATUS FOR LOCATING BODY CAVITIES

This is a continuation of application Ser. No. 559,757, now abandoned, filed Jul. 30, 1990 which is a divisional of copending application Ser. No. 310,366 now U.S. Pat. No. 4,944,724 filed on Feb. 13, 1989 which in turn is a continuation of application Ser. No. 07/058,400 filed on Jun. 5, 1987 and now abandoned.

BACKGROUND OF THE INVENTION

This invention relates generally to apparatus for draining fluids from body cavities and for introducing fluids into body cavities. More particularly, this invention relates to an improved apparatus for positively locating a body cavity having fluctuating fluid pressure and then either draining fluids from the cavity or introducing fluids into it.

An apparatus for draining fluids from body cavities, including particularly the pleural cavity, is described in U.S. Pat. No. 4,664,660. The apparatus described in that patent includes a vented housing having a fluid-receiving chamber, an anti-reflux valve mounted within the housing and a catheter, extending from the housing, in communication with the chamber through the anti-reflux valve.

The apparatus of U.S. Pat. No. 4,664,660 is used in the drainage of fluids from the pleural cavity by inserting a solid trocar into the end of the catheter. A skin incision is then prepared and the trocar/catheter assembly is introduced into the pleural space through the incision. When the trocar is removed from the catheter, fluid drains from the pleural cavity through the catheter and the vented housing.

While the above-described apparatus represents a very important contribution to the art, in using it one cannot ascertain whether the open distal end of the trocar/catheter assembly is properly located in the pleural cavity until the trocar is removed. Since drainage cannot begin until the trocar is removed, the proper positioning of the catheter in the pleural space cannot be determined with the trocar in place. In addition, damage to the lung, heart and surrounding tissue could occur if the trocar is not removed as soon as the tip of the trocar catheter assembly enters the pleural space.

Another apparatus for draining fluids from body cavities, particularly aspiration of liquids from the pleural cavity, is disclosed in U.S. Pat. No. 4,447,235. The apparatus described in this patent includes a catheter/hollow needle assembly which is inserted into the pleural cavity. During the insertion procedure, a vacuum is maintained in the needle with a syringe so that liquid will enter the syringe for observation by the surgeon when the needle enters the pleural space. This device cannot function unless a vacuum is maintained. Also, it cannot signal subsequent dislocation of the catheter from the pleural space or completion of drainage since the syringe is disconnected (and cannot be reintroduced) after the initial insertion of the catheter in the pleural cavity.

A medical suction device with an indicator flag to signal the pressure being developed by the device is described in U.S. Pat. No. 4,404,924. The indicator flag is designed to stand upright when the pressure in the device is relatively high and to collapse when suction is developed. The flag, unfortunately, indicates the state of fill of the suction device, not the satisfactory location of a catheter in the body cavity being aspirated or the completion of the aspiration procedure. In addition, it has no application in a procedure conducted without vacuum assistance.

Finally, U.S. Pat. No. 4,164,938 describes a device for diagnosing the presence of a tension pneumothorax. This device includes a sleeve with a needle at one end for puncturing the chest wall and extending into the pleural cavity and a diaphragm at the other end which expands when the pressure in the pleural cavity is greater than atmospheric. Since this device does not vent fluid from the pleural cavity, the diaphragm does not provide any indication that venting is proceeding or that the pneumothorax has been resolved.

SUMMARY OF THE INVENTION

It is therefore an object of the present invention to provide an apparatus for draining fluids from a body cavity or introducing fluids into the cavity which positively locates the body cavity.

It is a further object of the present invention to provide a catheter apparatus in which a trocar is used to facilitate insertion of the catheter into the cavity, and in which a positive indication that the cavity has been located is provided without removing the trocar.

It is yet another object of the present invention to provide a catheter apparatus for draining fluids from a body cavity which permits the drainage to commence as soon as the apparatus enters the cavity.

These and other objects of the present invention will be apparent from the discussion below.

The present invention is therefore directed to an apparatus for transporting fluid either into or out of a body cavity having a fluctuating fluid pressure. The apparatus includes a conduit for entering the cavity, means for signaling the fluctuation of the fluid pressure in the cavity and means for transporting the fluid either into or out of the cavity. The signaling means provides a positive indication that the cavity has been located.

In one important embodiment, the means for entering the cavity comprises a catheter and a housing, having an inlet chamber and a discharge chamber, supporting the catheter in sealed fluid communication with the inlet chamber. An inlet port is provided in the housing having a seal for reversibly receiving a trocar and enabling at least a portion of the trocar to pass through the inlet chamber and the catheter. The inlet port seal is adapted for sealing the chamber both in the absence of the trocar and upon its insertion and withdrawal. In addition, an anti-reflux valve is mounted in the housing, coupling the inlet chamber to the discharge chamber. The anti-reflux valve permits fluid entering the inlet chamber to pass into the discharge chamber, but prevents any fluid from flowing back into the inlet chamber. Finally, and most importantly, this embodiment of the invention also includes means for signaling the fluctuating fluid pressure in the body cavity, to thereby positively signal that the body cavity has been located.

In another important embodiment of the invention an improvement in apparatus having a conduit with a removable trocar to aid body penetration is provided. The improvement comprises a furrow in the trocar which permits fluid flow through the conduit while the trocar is still in place in the conduit.

BRIEF DESCRIPTION OF THE DRAWINGS

The features of this invention which are believed to be novel are set forth with particularly in the appended claims. The invention, together with its objects and the advantages thereof, may be best understood by reference to the following description, taken in conjunction with the accompanying drawings, in which like reference numerals identify like elements in the several figures and in which:

FIG. 1 is a perspective view of an apparatus in accordance with the present invention, showing a trocar inserted into the inlet chamber of the apparatus;

FIG. 1A is an elevation view of the rear of the apparatus of FIG. 1;

FIG. 2 is a sectional view of the apparatus of FIG. 1, taken along lines 2—2 of FIG. 1A;

FIG. 2A is a partial sectional view of a discharge chamber of an alternate embodiment of the apparatus of FIG. 1 in which a discharge port is provided for removing liquids from the discharge chamber;

FIG. 2B is a partial sectional view of an alternate embodiment of the apparatus of FIG. 1 in which an auditory signal indicative of the fluctuation of fluid pressure is produced;

FIG. 3 is a plan view of the film valve utilized in the apparatus of FIG. 1;

FIG. 4A is a front elevation view of a furrowed trocar used in the practice of the present invention;

FIG. 4B is an enlarged sectional a view of the trocar of FIG. 4, taken along lines 4B—4B. of FIG. 4; and FIGS. 5A and 5B are enlarged sectional views of the domed signal utilized in the apparatus of FIG. 1.

DESCRIPTION OF THE PREFERRED EMBODIMENTS

The apparatus of the present invention is intended to have application in locating and in moving fluids either into or out of body cavities such as the pleural cavity, the signal epidural space, blood vessels, the gallbladder, the urinary bladder, the kidney pelvis, the brain ventricles and the brain subdural and epidural spaces. However, for purposes of illustration, the discussion below is directed primarily to an embodiment of the invention particularly suited for locating and draining fluids from the pleural cavity.

An apparatus 10 in accordance with the present invention is illustrated in FIGS. 1, 1A and 2. The apparatus includes a housing 12 having an inlet chamber 14 and a discharge chamber 16. Housing 12 is made of any rigid, impervious material, such as an acrylic, ABS, polystyrene or polyvinyl chloride plastic.

Apparatus 10 includes a manifold 17 having a first bore 18 extending through the manifold. Bore 18 is enlarged at its distal end to form a recess 20 to which a cannula 22 is affixed and sealed. A polyethylene are one preferred material. When this laminate is used, the plastic film is used with the polyethylene sides facing each other.

The edges of the two film members of the valve are heat sealed to each other with a tortuous profile 42 at the closed edges of the valve in order to prevent fluid leakage. The cracking resistance or threshold pressure at which the valve permits fluid to flow through it can be adjusted by varying the thickness of the plastic films and the length and width of the valve passage 43.

Other anti-reflux valves which are sufficiently sensitive to reflux pressures to produce a discernible movement in the signaling means (described below) can be used. The "Heimlich valve" utilized in U.S. Pat. No. 4,664,660, described above in the Background of the Invention, for example, can be used in the present application but is less preferred than the film valve, because the Heimlich valve is far less sensitive to reflux pressures. The Heimlich valve is described in U.S. Pat. No. 3,463,159.

The space defined by bore 18 and bore 34 together comprise the inlet chamber 14 of the apparatus. The inlet chamber is separated from outlet chamber 16 by anti-reflux valve 40.

Catheter 24 is formed of a stainless steel spring core 48 covered with an elastomer 50, which preferably is present in the form of a silicone coating on the spring. The tip 52 of the catheter is preferably made of a resilient polymer, such as polyurethane or silicone rubber, and is bonded to the end of the spring core.

The tip of the catheter is open at 54 to permit trocar 28 to pass through. Elastomer covering 50 of the catheter may have a plurality of ports 56, in addition to the opening at the tip, to facilitate draining between the exposed coils of spring 48, and to insure that drainage proceeds in the event that opening 54 is blocked by expanding lung tissue.

Discharge chamber 16 has a series of elongated vent openings 58 (FIG. 1A) located behind a protective cover 59. Cover 59 is affixed to housing 12 along its sides and undercut to create a passages 61 at its top and bottom through which gaseous fluids vent to the atmosphere. A hydrophobic filter 60 is fixed in place behind the vent openings to prevent aqueous liquids from escaping the discharge chamber.

A self-adhesive strip 62 is attached to the exterior of the distal wall 64 of housing 12. The adhesive strip is covered by a protective release sheet 66 which is removed prior to installation of the catheter, so that the strip can be applied to the patient's skin upon installation of the apparatus.

In addition, a seal cuff 68 is provided about catheter 24, adjacent wall 64 of the apparatus which will abut the patient's body. Cuff 68, which is preferably a sponge silicone or other resilient material, is intended to prevent tissue emphysema by sealing the perimeter of the catheter at the wound site where the catheter enters the body.

An absorbent pad 70 is positioned at the bottom and side of the discharge chamber to absorb small quantities of blood or other liquids which may pass through the apparatus when, as in the present embodiment, the principal fluid being drained is air. In an alternative embodiment, where significant amounts of liquid are to be drained, a collection port 72 (FIG. 2A) is provided so that the fluid may be continuously withdrawn either under suction or by gravity.

Trocar 28, which is illustrated in FIGS. 4A and 4B, includes a handle 74 molded or bonded to its proximal end. The trocar is sized so that its distal, pointed tip 76 protrudes beyond the tip 52 of catheter 24 when the trocar is fully inserted in the apparatus. Trocar 28 includes a furrow 78 which extends from trocar tip 76 through a point 79 near handle 74. The furrow permits fluid communication between the tip 52 of the catheter and inlet chamber 34 while the trocar is inserted in the catheter. Furrow 78 thus permits fluids to be vented from the plural cavity immediately upon introduction of the catheter, without removal of the trocar. Furrow 78 also permits the signaling means (described below) to being functioning immediately upon entry of the catheter tip into the pleural cavity.

Means for signaling fluctuation of fluid pressure in the pleural cavity is provided in the form of a resilient signal dome 80 which is in fluid communication with inlet chamber 14 by way of bore 82 in manifold 17. Signal dome 80 has an annular lip 84 which is sealingly affixed to the top 36 of manifold 17 so that the dome caps and closes off bore 82. A clear cover 86 is affixed to the top 36 of manifold 17, to define a signal chamber 88. A vent hole 90 is formed in the cap to permit the signal dome to freely expand and contract within it.

Signal dome 80 is made of a resilient material, preferably silicone, with a shape and resilience such that the dome will collapse (FIG. 5B) and return to its normal configuration (FIG. 5A) with the fluctuating pressures in the pleural cavity, producing a pulsating visual indication of the pleural cavity pressures. In the embodiment illustrated, the signal dome is molded of silicone and is wider than it is high. It has a wall thickness of about 0.012 to 0.015 inches at its base tapering to about 0.007 inches at its apex, as illustrated in FIGS. 5A–5B. In other applications the signal dome sensitivity may be adjusted as necessary by varying, for example, the material from which the signal dome is fabricated, as well as the size and shape of the dome, and its wall thickness and taper.

The functioning of the signal means depends on: 1) changes in pressure (differential pressures) in the body cavity of interest; 2) cracking resistance of the anti-reflux valve, and 3) sensitivity of the signal dome. Since the differential pressures of the body cavity are not controllable, the anti-reflux valve cracking resistance and/or the signal dome sensitivity must be matched to the differential pressures of the particular body cavity in order to produce the desired pulsating movement in the signal dome. For example, in an application in the epidural space, where the pressures are generally lower than in the pleural cavity, a more sensitive dome and/or an anti-reflux valve with a higher cracking resistance will be needed.

Naturally, the signaling means include any resilient structures which pulsate with fluctuating pressure in the system. For example, a flat resilient membrane which expands with increasing pressure and collapses back to a generally flat position on decreasing pressure would provide a satisfactory alternative to the signal dome illustrated above.

In an alternate embodiment, an auditory signal is provided, either alone or in conjunction with the visual signal described above. Thus, there is illustrated in FIG. 2B an embodiment in which a hole 92 is made in cover 59, passages 61 are closed off and a low velocity whistle 94 is affixed to the cover so that the opening in the whistle 96 is aligned with the hole in cover 59. Thus, the air passing though the discharge chamber will exit through the whistle, producing a rhythmic auditory signal indicative of the fluctuating pressure in the pleural cavity before the pneumothorax is resolved and either a continuous signal or silence when the pneumothorax is resolved. The loudness and sensitivity of the signal will be a function of the cracking resistance of the anti-reflux valve 40, the resistance to air movement of filter 60, and the sensitivity of the whistle.

In yet another alternative embodiment of the present invention, once the catheter is in place in the pleural cavity, a cannula sized to fit within the catheter 24 is passed through seal 30, through bore 18 and into the catheter. A vacuum is then applied to the cannula to rapidly remove fluids from the pleural space.

In treating traumatic or idiopathic pneumothorax, or for evacuating air from the chest following thoracic surgery or percutaneous lung biopsy, the apparatus 10 may be used as follow:

1. If the apparatus is supplied in sterile kit form, the apparatus is removed from the kit under sterile conditions and the trocar is inserted through inlet port 26 so that its tip protrudes from the tip 52 of catheter 24.
2. A site is selected, preferably in the second interspace at the midclavicular line.
3. The site is prepared with an antimicrobial agent and a drape is placed over the site.
4. Local anesthesia is applied at the site.
5. Using a scalpel, a small skin incision is made at the site.
6. The release sheet is removed from the adhesive strip.
7. With the thumb over the trocar handle, the device is positioned at the incision and the trocar/catheter assembly is passed into the pleural space immediately above the superior border of the rib. Catheter 24 is maintained in a straight condition by the trocar, so that the catheter will remain rigid and resist bending upon insertion into the body cavity. In addition, spring 48 prevents any significant compaction of the catheter on the trocar during the insertion process.
8. When the catheter tip enters the pleural space, signal dome 80 will begin to pulsate. When this occurs, the trocar is removed to increase the rate of fluid flow and prevent damage to the lung. The continuing pulsating movement of the signal dome is observed as the air is evacuated from the pleural cavity and the lung begins to reinflate.
9. When the pneumothorax is resolved and the lung is reinflated the signal dome stops pulsating and the apparatus can be removed.

While the present apparatus has been described in connection with the removal of fluids from the pleural cavity, the device may be used in a multitude of other applications, both for removing fluids and for introducing fluids. For example, it may be used in locating and in moving fluids either into or out of body cavities such as the pleural cavity, the signal epidural space, blood vessels, the gall bladder, the urinary bladder, the kidney pelvis, the brain ventricles, and the brain subdural and epidural spaces. In introducing fluids, the catheter is inserted in the cavity and then a cannula is introduced through seal 30 and into the catheter, whereby the fluids to be introduced are passed through the cannula by way of a syringe or other conventional injection device.

For example, in administering an epidural block, the anesthesiologist would position the trocar/catheter tip in the epidural space relying upon the pulsating signal dome to positively indicate that the epidural space has been located. He or she would then remove the trocar and insert a syringe containing an appropriate anesthetic and inject the anesthetic into the epidural space.

While particular embodiments of the invention have been shown and described, it will be obvious to those skilled in the art that various changes and modifications may be made therein without departing from the spirit and scope of the invention and, therefore, it is intended in the appended claims to cover all such changes and modifications which fall within the true spirit and scope of the invention.

What we claim is:

1. An apparatus for locating a body cavity having a fluctuating fluid pressure and transporting fluid either into or out of the cavity comprising:

a conduit comprising a flexible catheter having a spring covered by an elastomeric coating for entering the cavity;

means, in communication with said conduit, for producing a pulsating indication corresponding to the fluctuation of the fluid pressure in the cavity when said conduit enters the body cavity; and means, in communication with said conduit, for transporting fluid either into or out of the cavity.

2. The apparatus of claim 1 wherein said conduit serves as said transporting means.

3. The apparatus of claim 1 wherein said signaling means comprises an elastomeric element which pulsates in response to the fluctuating fluid pressure in the body cavity.

4. An apparatus for locating a body cavity having a fluctuating fluid pressure and transporting fluid either in or out of the cavity comprising:

a conduit;

a housing having an inlet chamber and a discharge chamber, said housing supporting said conduit in sealed fluid communication with said inlet chamber;

an inlet port in said housing having inlet port sealing means for reversibly receiving a trocar and enabling at least a portion of a trocar to pass through said inlet chamber and said conduit, said inlet port sealing means being adapted for sealing said chamber both in the absence of a trocar and upon insertion and withdrawal of a trocar, anti-reflux valve means mounted in said housing, coupling said inlet chamber with said discharge chamber, for permitting fluid entering said inlet chamber to pass into said discharge chamber while preventing fluid from flowing from said discharge chamber into said inlet chamber and means for producing a pulsating visual indication corresponding to the fluctuating fluid pressure in the body cavity upon entry of the conduit into a body cavity.

5. The apparatus of claim 4 including a trocar positioned in said inlet port and passing through said inlet chamber and said conduit, said trocar having a furrow which permits fluid flow through said conduit and said inlet chamber.

6. The apparatus of claim 4 wherein said conduit is a flexible catheter comprising a spring covered by an elastomeric coating.

7. The apparatus of claim 4 wherein a resilient cuff is provided at the base of said conduit to seal against the body.

8. The apparatus of claim 4 wherein said anti-reflux valve is a film valve comprising two pieces of plastic film closed along their edges.

9. The apparatus of claim 8 wherein said closed edges of said film valve have a tortuous profile.

10. The apparatus of claim 8 wherein said plastic film pieces comprise a nylon/polyethylene laminate.

11. The apparatus of claim 4 wherein a collection port is provided in said discharge chamber for withdrawing liquids therefrom.

12. The apparatus of claim 4 wherein said signaling means comprises an elastomeric element which pulsates in response to the fluctuating fluid pressure in the body cavity.

13. The apparatus of claim 12 wherein said elastomeric element is dome-shaped and the thickness of the wall of said dome-shaped elastomeric element gradually tapers to its apex.

14. The apparatus of claim 4 wherein said signaling means comprises a whistle.

15. The apparatus of claim 4 including a cannula passing through said inlet port sealing means and said inlet chamber and into said conduit for transporting fluid either into or out of the cavity.

* * * * *

UNITED STATES PATENT AND TRADEMARK OFFICE
CERTIFICATE OF CORRECTION

PATENT NO. : 5,356,386
DATED : Oct. 18, 1994
INVENTOR(S) : Edward M. Goldberg, Glencoe; Lev Melinyshyn, Mt. Prospect; Michael Jaron, Des Plaines; Jeffrey M. Stupar, Chicago; all of Ill.

It is certified that error appears in the above-indentified patent and that said Letters Patent is hereby corrected as shown below:

In Col. 1, line 29, after the word "the", (1st occurrence) insert --catheter so that the sharp tip of the trocar extends beyond the distal--.

In Col. 2, line 67, substitute --particularity-- for "particularly".

In Col. 3, line 35, substitute --spinal-- for "signal".

Signed and Sealed this

Fourteenth Day of February, 1995

Attest:

BRUCE LEHMAN

Attesting Officer

Commissioner of Patents and Trademarks